United States Patent [19]

Inoue et al.

[11] 4,301,299

[45] Nov. 17, 1981

[54] SYNTHESIS OF UREA

[75] Inventors: Shigeru Inoue, Kamakura; Hiroshi Ono, Fujisawa, both of Japan

[73] Assignee: Toyo Engineering Corporation, Tokyo, Japan

[21] Appl. No.: 203,595

[22] Filed: Nov. 3, 1980

[30] Foreign Application Priority Data

Oct. 8, 1979 [JP] Japan ............... 54/128860

[51] Int. Cl.³ ............ C07C 126/02; C07C 126/08
[52] U.S. Cl. ............................ 564/67; 564/68; 564/70; 564/72
[58] Field of Search ............... 564/67, 70, 72

[56] References Cited

U.S. PATENT DOCUMENTS

| 2,212,847 | 8/1940 | Porter | 564/67 |
| 3,317,601 | 5/1967 | Otsuka et al. | 564/67 |
| 3,876,696 | 4/1975 | Guadalupi et al. | 564/70 |

FOREIGN PATENT DOCUMENTS

| 42-26770 | 12/1967 | Japan | 564/70 |
| 1031528 | 6/1966 | United Kingdom | 564/70 |
| 1185944 | 3/1970 | United Kingdom | 564/67 |
| 244332 | 10/1969 | U.S.S.R. | 564/67 |
| 452558 | 3/1975 | U.S.S.R. | 564/67 |

Primary Examiner—John Doll

[57] ABSTRACT

A process for synthesizing urea in which a urea synthesis effluent obtained by reacting carbon dioxide and ammonia at urea synthesis pressures and temperatures is subjected to stripping treatment with carbon dioxide under pressures substantially equal to urea synthesis pressures to separate the unreacted carbon dioxide and ammonia contained in the urea synthesis effluent as a gaseous mixture, and a sufficient amount of said gaseous mixture to maintain the urea synthesis temperatures at a predetermined level is recycled to the urea synthesis in the gaseous state, the balance being subjected to condensation to be recycled in the liquid state to the urea synthesis.

13 Claims, 2 Drawing Figures

SYNTHESIS OF UREA

BACKGROUND OF THE INVENTION

1. Field of the Invention

This invention relates to a novel and improved process for the synthesis of urea, and more particularly, it relates to an improvement in a process wherein the separation of unreacted carbon dioxide and ammonia (hereinafter referred to as unreacted materials) from a urea synthesis effluent is effected under a pressure equal to urea synthesis pressures, and a gaseous mixture of the separated carbon dioxide and ammonia is recycled to urea synthesis for reuse.

2. Description of the Prior Art

In the case where the unreacted materials are separated from the urea synthesis effluent and recovered to be recycled to urea synthesis for reuse under pressures substantially equal to urea synthesis pressures, it is common practice that the separation of the unreacted materials is promoted by the stripping thereof with carbon dioxide. A gaseous mixture of the unreacted materials thus separated is recovered by condensing the gaseous mixture to form ammonium carbamate, and heat generated is removed by means of producing steam. Generally, the condensation of the gaseous mixture is not effected completely, so that after the step of removing heat generated the unreacted materials thus recovered are recycled to urea synthesis as a mixture of an ammonium carbamate solution and an uncondensed gaseous mixture. As described above, the gaseous mixture is not completely condensed, so that the uncondensed part of the gaseous mixture may be condensed in a urea synthesis autoclave to generate heat and heat balance in the urea synthesis autoclave may be maintained.

There are two proposed methods of recycling the unreacted materials thus recovered to the urea synthesis autoclave: a gravity flow metod, in which the unreacted materials thus recovered are allowed to flow downwards due to a gravity head thereof, and another method, in which a fluid other than the unreacted materials, for example, ammonia is pressurized to an elevated pressure, so that the high pressure ammonia may be used as a driving medium for operating an ejector, and the unreacted materials may be introduced into the urea synthesis autoclave by aspiration action of the ejector. The gravity flow method has such disadvantages as the need for a great difference in height between a position where the unreacted materials are recycled and a condenser for the unreacted materials, that it is not always possible to recycle the unreacted materials thus recovered, which consist of a mixture of a liquid phase and a gas phase a specific gravity different from each other, to the urea synthesis autoclave at constantly uniform rate. Another drawback is that unstable operation conditions are resulting among the urea synthesis autoclave, a separator for the unreacted materials or stripper, and a condenser for the unreacted materials. On the other hand, the method with the ejector has the disadvantage that as the ratio of gas phase to liquid phase in the phase mixture is increased, the driving fluid is required to be pressurized to an extremely high pressure so that the ejector might be able to operate, resulting in necessity for more power.

In the condenser for the unreacted materials, a portion of the unreacted materials is not condensed in order to maintain the heat balance in the urea synthesis autoclave as described above. However, the following processes are further proposed, in which the heat balance in the urea synthesis autoclave can be maintained even if no gaseous phase remains in the unreacted materials recovered in the condenser for the unreacted materials. According to one proposed process, a sufficient amount of make-up carbon dioxide for maintaining the heat balance in the urea synthesis autoclave is fed directly to the urea synthesis autoclave, and the balance is used for stripping the unreacted materials, and substantially all of the gaseous mixture of the unreacted materials thus obtained is condensed to be recycled as liquid to the urea synthesis autoclave for reuse. According to another process, the unreacted materials are separated in two stages under pressures equal to each other, that is, a gaseous mixture of the unreacted materials separated in a first stage is recycled directly to the urea synthesis autoclave, and substantially all of the gaseous mixture of the unreacted materials separated in a second stage is condensed to be recycled as liquid to the urea synthesis autoclave for reuse.

However, these two processes described above have the following problems: with respect to separation of the unreacted materials, according to the former process, separation of the unreacted materials will not always be effected as desired due to restrictions in the amount of carbon dioxide usable for stripping, and according to the latter process, it is necessary to keep a balance between the amount of the unreacted materials separated in the first stage and that in the second stage in order to obtain a gaseous mixture in the first stage in the proper amount required for maintaining heat balance in the urea synthesis autoclave, since there is a possibility of it becoming unstable particularly for operations in the second stage.

SUMMARY OF THE INVENTION

It is an object of this invention to provide a process for the synthesis of urea including improved steps for separating and recovering unreacted materials.

It is another object of this invention to provide a process for the synthesis of urea, in which urea synthesis temperatures can be maintained at a predetermined level.

It is a further object of this invention to provide a process for the synthesis of urea, in which the unreacted materials can readily be recycled to the urea synthesis.

The above objects of this invention are attained by a process for synthesizing urea as described below:

A process for synthesizing urea which comprises reacting carbon dioxide and ammonia in a urea synthesis zone at urea synthesis pressures and temperatures, separating unreacted carbon dioxide and ammonia from the resultant urea synthesis effluent as a gaseous mixture under pressures substantially equal to said urea synthesis pressures, recycling a sufficient amount of said gaseous mixture to maintain said urea synthesis temperatures at a predetermined level to said urea synthesis zone in the gaseous state, and subjecting the balance to condensation under pressures substantially equal to said urea synthesis pressures for recycle to said urea synthesis zone in the liquid state.

DETAILED DESCRIPTION OF THE INVENTION

Figure 1:
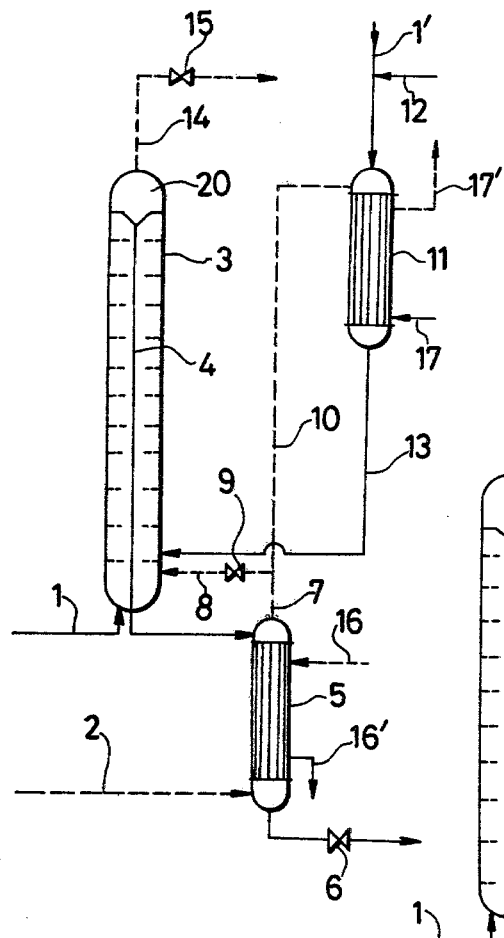
FIG. 1 is a flow sheet showing an embodiment of this invention.

In the present invention, the unreacted materials may be separated in two stages. In the first stage excess ammonia contained in the urea synthesis effluent is separated under pressures substantially equal to urea synthesis pressures, and in the second stage, unreacted carbon dioxide and ammonia are separated as a gaseous mixture under pressures substantially equal to urea synthesis pressures.

The excess ammonia thus separated and a portion of the gaseous mixture are recycled in the gaseous state to the urea synthesis zone at pressures substantially equal to the urea synthesis pressures, so that the temperature in the urea synthesis zone may be maintained at a predetermined level.

Alternatively, the separation of the unreacted materials according to the present invention is preferably effected by stripping with the total amount of carbon dioxide to be freshly fed to the urea synthesis autoclave. When the amount of the unreacted materials in the urea synthesis zone is too small to be stripped with the total amount of the make-up carbon dioxide, a portion of the make-up carbon dioxide may be used for stripping, and the balance may be introduced directly into a condenser for the unreacted materials. Further, the amount of the gaseous mixture introduced into the urea synthesis autoclave is preferably increased or decreased in response to a change in temperature in the urea synthesis zone, so that the urea synthesis temperatures may be held at a predetermined level. That is, when the temperature in the urea synthesis zone is lower than a predetermined temperature, a recycle amount of the gaseous mixture is increased, and conversely, thereto when higher than the predetermined temperature, the recycle amount is decreased. The recycle amount is controlled by manually or automatically adjusting a suitable control valve.

The recycle amount of the gaseous mixture to the urea synthesis zone cannot easily be determined because operation conditions in the respective stages are intertwined with one another, but when the total amount of the make-up carbon dioxide is used for stripping of the unreacted materials to increase the degree of separation of the unreacted materials as much as possible and to increase operating temperatures of the condenser for the unreacted materials as much as possible, a factor, which has a great effect on the recycle amount, is the molar ratio of ammonia to carbon dioxide in urea synthesis (the molar ratio being preferably in the range of from 2 to 5 in the present invention). Under such conditions as above, the molar ratio of ammonia to carbon dioxide in the gaseous mixture of unreacted materials recycled to the urea synthesis zone is preferably in the range of from 0.9 to 1.8.

Further, a process, in which a greater part of the heat required for maintaining the urea synthesis zone at a predetermined temperature level relies on a gaseous mixture introduced directly to the urea synthesis zone and the balance relies on a preheating temperature of the make-up liquid ammonia, is apparently applicable. That is, the amount of the gaseous mixture introduced directly to the urea synthesis zone is maintained constant, and the temperature in the urea synthesis zone is adjusted by changing the preheating temperature of liquid ammonia. In this case, the greater part of heat required therefor is fed from the gaseous mixture, and stability for operations among the urea synthesis autoclave, stripper and ammonium carbamate condenser is not disturbed, but operations in ammonium carbamate condenser are rather stabilized.

Specific embodiments of the present invention will be particularly described hereinafter with reference to the accompanying drawings. A process shown in FIG. 1 is suitable in the case where an ammonia to carbon dioxide molar ratio is relatively low (for example, where the ratio is in the neighborhood of 3). Liquid ammonia from line 1, recovered ammonium carbamate solution from line 13, and a part of the gaseous mixture of unreacted materials from line 8 are introduced into the urea synthesis autoclave 3 respectively to be reacted at a temperature in the range of 170° to 210° C., particularly 180° to 205° C. and a pressure in the range of 120 to 250 kg/cm$^2$ G. After completion of the reaction, the urea synthesis effluent obtained is separated at the top 20 of the urea synthesis autoclave from an inert gas contained in feed materials and is withdrawn through tube 4, while the inert gas is discharged via line 14 and the pressure regulating valve 15, and ammonia and carbon dioxide contained therein are recovered in a suitable manner. The urea synthesis effluent is introduced at the top of the stripper 5 and flows downwards forming a thin film on the inner wall of heat transfer tubes in the stripper, while being heated to a temperature of from 180° to 230° C. with a high pressure steam which is introduced from line 16 and is discharged from line 16'. The urea synthesis effluent is brought into contact with carbon dioxide freshly fed from line 2, so that the unreacted materials contained therein may be separated by the stripping action of carbon dioxide, while flowing downwards as described above. The urea synthesis effluent is discharged through the pressure reducing valve 6 and is passed to a low pressure decomposition and recovery system (not shown), so that residual unreacted materials may be separated and recovered by the conventional procedure. A gaseous mixture separated at the stripper 5 is withdrawn from line 7, a portion of which is passed into the bottom of the urea synthesis autoclave 3 via a control valve 9 and line 8 to hold the temperature in the urea synthesis autoclave at a predetermined level by the heat of condensation thereof, and the balance is introduced into ammonium carbamate condenser 11 from line 10 and is brought into contact with aqueous ammonium carbamate solution, which is fed from a low pressure recovery system and is introduced from line 12, and liquid ammonia introduced from line 1' to be subjected to condensation for absorption, where the sum of the amounts of ammonia from line 1' and from line 1 is equal to the amount of the make-up ammonia. Heat generated therein is removed by evaporating the water introduced from line 17, so that the outlet temperature of the ammonium carbamate condenser may be maintained in the range of 160° to 200° C. The resulting steam is low pressure steam having a pressure lower than 7 kg/cm$^2$ G. The gaseous mixture is substantially completely condensed to the liquid phase when no or slight amount of inert gas is contained therein. Otherwise, the condensation remains incomplete, and some uncondensed gaseous mixture is formed with the result that the amount of the gaseous mixture introduced directly to the urea synthesis autoclave from line 8 is decreased by an amount corresponding to the amount of the uncondensed gaseous mixture thus formed. An ammonium carbamate solution produced in ammonium carbamate condenser 11 is passed into the bottom of the urea synthesis autoclave via line 13. The recycle of the ammonium carbamate solution can be effected by the gravity flow method, or with an ejector or pump. The pumping method is especially advantageous in that no gravity head between the urea synthesis autoclave and the ammonium carbamate condenser is required, and that the power required may be less compared with that with the ejector.

When a change in temperature at the outlet portion of the urea synthesis autoclave takes place due to some reasons, the opening of the control valve 9 is increased or decreased automatically or manually in response to the temperature change, whereby the recycle amount of the gaseous mixture to the urea synthesis, autoclave is regulated to maintain the temperature in the urea synthesis autoclave at a predetermined level. The urea synthesis autoclave is not provided with heating and cooling means.

Figure 2:
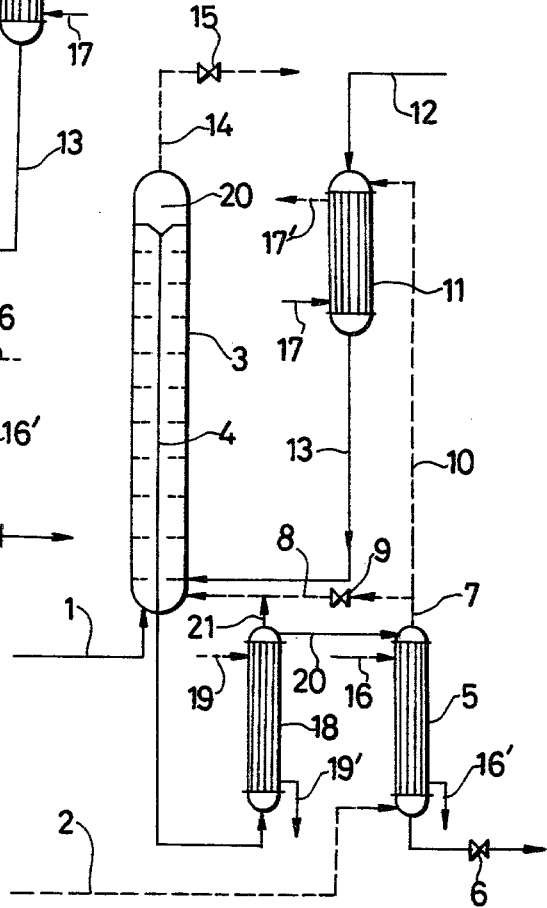
FIG. 2 is a flow sheet showing another embodiment of this invention.

A process shown in FIG. 2 is suitable for the case where an ammonia to carbon dioxide molar ratio in the urea synthesis autoclave is relatively high, for example, above 3.5. The above process is almost similar to that shown in FIG. 1 except that separation of unreacted materials is effected in two stages, so that only different portions from the process in FIG. 1 will be described hereinafter. The urea synthesis effluent withdrawn from line 4 is introduced into ammonia separator 18, and flows downwards forming a thin film on the inner wall of the heat transfer tubes therein, while being heated with high pressure steam, which is introduced from line 19 and discharged from line 19', during which a portion of excess ammonia is separated and the composition of the residual urea synthesis effluent is regulated, so that the ammonia to carbon dioxide molar ratio may be in the neighborhood of that of the urea synthesis effluent in the process shown in FIG. 1. The urea synthesis effluent withdrawn from ammonia separator 18 is passed into stripper 5 via line 20, and is processed in the same manner as in the process shown in FIG. 1. A portion of the gaseous mixture of the unreacted materials thus separated is introduced into the bottom of the urea synthesis autoclave along with excess ammonia, which is separated in ammonia separator 18 and withdrawn therefrom via line 21. The balance of the gaseous mixture is introduced into ammonium carbamate condenser 11 and is processed in the same manner as in the process shown in FIG. 1, except that the introduction of liquid ammonia from line 1' as in the process shown in FIG. 1 is not effected. The total amount of the make-up ammonia is introduced into the urea synthesis autoclave from line 1. The amount of the gaseous mixture introduced directly to the urea synthesis autoclave is regulated by regulating the opening of control valve 9 in response to the temperature at the outlet portion of the urea synthesis autoclave in the same manner as in the process shown in FIG. 1.

The present invention has the following advantages:
(1) Unstable operation conditions among urea synthesis autoclave, stripper, and ammonium carbamate condenser are avoided.
(2) The separation of the unreacted materials from the urea synthesis effluent can be effected by stripping with the total amount of the make-up carbon dioxide. As a result, the degree of the separation of the unreacted materials can be increased.
(3) When no or slight amount, of inert gas is present in the gaseous mixture passed to the ammonium carbamate condenser, the condensation of the gaseous mixture is effected completely, so that the recycle of the condensed liquid to the urea synthesis autoclave can readily be carried out with a pump as well as by a gravity flow method or with an ejector.
(4) The temperature of the urea synthesis autoclave can readily be maintained at a constant level.

The present invention will be illustrated by the following Examples which are understood not to be constituting a limitation of the invention.

EXAMPLE 1

This is an example where 40% excess ammonia is used. The urea synthesis effluent formed under the conditions of a pressure of 145 kg/cm$^2$ G and a temperature of 183° C., and composed of 1024.4 kg/hr of urea, 773.9 kg/hr of ammonia, 500.8 kg/hr of carbon dioxide and 614.6 kg/hr of water is introduced into the top of a stripper operated under a pressure of 145 kg/cm$^2$ G, and is brought into contact counter-currently with 751.2 kg/hr of carbon dioxide gas at 145° C. introduced from the bottom of stripper to separate a major part of the unreacted materials, while flowing downwards within the heat transfer tubes of the stripper under heating with high pressure steam of 25 kg/cm$^2$ G. The urea synthesis effluent withdrawn from the stripper is composed of 1024.4 kg/hr of urea, 119.5 kg/hr of ammonia, 102.4 kg/hr of carbon dioxide and 495.1 kg/hr of water, and is subjected to low pressure decomposition and recovery, and then to a purification step by the conventional procedure. On the other hand, a gaseous mixture of carbon dioxide introduced into the stripper and the unreacted materials thus separated is composed of 654.4 kg/hr of ammonia, 1149.6 kg/hr of carbon dioxide and 119.5 kg/hr of water, and is discharged from the top of the stripper at a temperature of 185° C. In order to maintain the temperature of the urea synthesis autoclave at 183° C., 27% by weight of the gaseous mixture thus separated, that is, 176.5 kg/hr of ammonia, 310.4 kg/hr of carbon dioxide and 32.3 kg/hr of water are introduced directly to the urea synthesis autoclave. The balance, 73% by weight thereof, that is, 477.9 kg/hr of ammonia, 839.2 kg/hr of carbon dioxide and 87.3 kg/hr of water is passed to an ammonium carbamate condenser, into which an aqueous ammonium carbamate solution at 60° C. which is fed from the low pressure recovery system and is composed of 119.5 kg/hr of ammonia, 102.4 kg/hr of carbon dioxide and 187.7 kg/hr of water, and 290.2 kg/hr of the make-up ammonia, that is, a part thereof are fed at 36° C. under pressure, and the balance of the gaseous mixture is condensed completely. The condensation temperature is 165° C. and heat generated by condensation is recovered as 954 kg/hr of 3.5 kg/cm$^2$ G saturated steam. The resultant concentrated ammonium carbamate solution is recycled to the bottom of the urea synthesis autoclave by gravity flow method. On the other hand, 290.2 kg/hr of the balance of the make-up ammonia other than those introduced into the ammonium carbamate condenser are fed to the urea synthesis autoclave under pressure. The operation condition in the urea synthesis autoclave, stripper and ammonium carbamate condenser are highly stabilized.

EXAMPLE 2

This is an example in the case where 100% excess ammonia is used. A urea synthesis effluent formed under the conditions of a pressure of 200 kg/cm$^2$ G and a temperature of 195° C., and composed of 1024.4 kg/hr of urea, 1115.5 kg/hr of ammonia, 343.8 kg/hr of carbon dioxide and 591.2 kg/hr of water is introduced into an ammonia separator in order to separate a portion of excess ammonia and heated with high pressure steam of 25 kg/cm² G under a pressure of 200 kg/cm² G to separate 415.3 kg/hr of ammonia, 34.5 kg/hr of carbon dioxide and 35.0 kg/hr of water at 205° C. The urea synthesis effluent withdrawn from the ammonia separator is then introduced into the top of a stripper operated under 200 kg/cm² G to separate the residual excess ammonia and unreacted materials in the same manner as in Example 1. An aqueous solution composed of 1024.4 kg/hr of urea, 122 kg/hr of ammonia, 102.4 kg/hr of water is obtained from the bottom of the stripper, depressurized to be subjected to low pressure decomposition and recovery, and then to a purification step by the conventional procedure.

On the other hand, from the top of the stripper a gaseous mixture composed of 578.2 kg/hr of ammonia, 958.1 kg/hr of carbon dioxide, and 66.2 kg/hr of water including the make-up carbon dioxide used for stripping is withdrawn at 205° C. A portion, 7.2% by weight, of the gaseous mixture, that is, 41.6 kg/hr of ammonia, 69.0 kg/hr of carbon dioxide and 4.8 kg/hr of water is introduced directly to the bottom of the urea synthesis autoclave along with a separated gas from the ammonia separator. The balance of the gaseous mixture, that is, the gaseous mixture composed of 536.6 kg/hr of ammonia, 889.1 kg/hr of carbon dioxide, and 61.4 kg/hr of water is introduced into the ammonium carbamate condenser, and an aqueous ammonium carbamate solution from the low pressure recovery system at 60° C., which is composed of 122 kg/hr of ammonia, 102.4 kg/hr of carbon dioxide and 182.7 kg/hr of water, is pressurized to an elevated pressure to be introduced thereto. The gaseous mixture introduced thereto is completely condensed, and the resultant concentrated ammonium carbamate solution has a temperature of 180° C. and is recycled to the bottom of the urea synthesis autoclave by the gravity flow method.

Further, 580.5 kg/hr of the ammonia is pressurized to an elevated pressure at 36° C. and is introduced into the bottom of the urea synthesis autoclave. The operation conditions in the urea synthesis autoclave, stripper, and ammonium carbamate condenser are highly stabilized.

What is claimed is:

1. A process for synthesizing urea which comprises reacting carbon dioxide and ammonia in a urea synthesis zone at urea synthesis pressures and temperatures, separating unreacted carbon dioxide and ammonia from the resultant urea synthesis effluent as a gaseous mixture under pressures substantially equal to said urea synthesis pressures, recycling a sufficient amount of said gaseous mixture to maintain said urea synthesis temperatures at a predetermined level to said urea synthesis zone in the gaseous state, and subjecting the balance to condensation under pressures substantially equal to said urea synthesis pressures for recycle in the liquid state to said urea synthesis zone.

2. A process as claimed in claim 1, wherein said unreacted carbon dioxide and ammonia are separated by stripping with the total amount of make-up carbon dioxide.

3. A process as claimed in claim 1, wherein the amount of said gaseous mixture recycled to said urea synthesis zone in the gaseous state is adjusted, so that said urea synthesis temperatures may be maintain at a predetermined level in response to a change in temperature in said urea synthesis zone.

4. A process as claimed in claim 1, wherein the ammonia to carbon dioxide molar ratio in said urea synthesis zone is in the range of 2 to 5.

5. A process as claimed in claim 4, wherein said ammonia to carbon dioxide molar ratio is about 3.

6. A process as claimed in claim 1, wherein temperature and pressure in said urea synthesis zone are in the range of 170° to 210° C. and 120 to 250 kg/cm² G, respectively.

7. A process as claimed in claim 1, wherein the separation of said unreacted carbon dioxide and ammonia is conducted at a temperature in the range of 180° to 230° C.

8. A process for synthesizing urea which comprises reacting carbon dioxide and stoichiometrically excess ammonia in a urea synthesis zone at urea synthesis pressures and temperatures, separating excess ammonia from the resultant urea synthesis effluent as ammonia gas under pressures substantially equal to said urea synthesis pressures, separating unreacted carbon dioxide and ammonia as a gaseous mixture from the urea synthesis effluent obtained by separating excess ammonia under pressures substantially equal to said urea synthesis pressures, recycling said excess ammonia separated as gaseous ammonia and a portion of said gaseous mixture to said urea synthesis zone to maintain the temperature in the urea synthesis zone at a predetermined level, and condensing substantially all of the balance of said gaseous mixture under pressures substantially equal to said urea synthesis pressures to be recycled in the liquid state to said urea synthesis zone.

9. A process as claimed in claim 8, wherein said unreacted carbon dioxide and ammonia are separated by stripping with the total amount of make-up carbon dioxide.

10. A process as claimed in claim 8, wherein the amount of said gaseous mixture recycled to said urea synthesis zone in the gaseous state is adjusted, so that said urea synthesis temperatures may be maintained at a predetermined level in response to a change in temperature in said urea synthesis zone.

11. A process as claimed in claim 8, wherein the ammonia to carbon dioxide molar ratio in said urea synthesis zone is 3.5 or higher.

12. A process as claimed in claim 8, wherein said excess ammonia is separated at a temperature of from 180° to 220° C.

13. A process as claimed in claim 8, wherein said unreacted carbon dioxide and ammonia are separated at a temperature of from 180° to 230° C.

* * * * *